US009795964B2

United States Patent
Smith et al.

(10) Patent No.: US 9,795,964 B2
(45) Date of Patent: Oct. 24, 2017

(54) DIRECT BOND TRANSFER LAYERS FOR MANUFACTURABLE SEALING OF MICROFLUIDIC CHIPS

(71) Applicant: International Business Machines Corporation, Armonk, NY (US)

(72) Inventors: Joshua T. Smith, Croton on Hudson, NY (US); Cornelia K. Tsang, Medford, MA (US); Chao Wang, Chandler, AZ (US); Benjamin H. Wunsch, Mt. Kisco, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 14/947,745

(22) Filed: Nov. 20, 2015

(65) Prior Publication Data

US 2017/0144149 A1    May 25, 2017

(51) Int. Cl.
*B29C 65/00* (2006.01)
*B31B 1/60* (2006.01)
(Continued)

(52) U.S. Cl.
CPC ... *B01L 3/502707* (2013.01); *B01L 3/502715* (2013.01); *B01L 3/502761* (2013.01); *B81B 7/0061* (2013.01); *B81C 1/00309* (2013.01); *G01N 15/10* (2013.01); *B01L 2200/0689* (2013.01); *B01L 2200/12* (2013.01); *B01L 2300/0887* (2013.01); *B01L 2300/0896* (2013.01); *B01L 2300/12* (2013.01); *B81B 2201/058* (2013.01);

(Continued)

(58) Field of Classification Search
CPC ...... H01L 21/20; B01L 3/00; B01L 3/502707; B01L 3/502715; B01L 3/502761; B29C 65/00; B31B 1/60; B32B 37/00
USPC ........... 438/478; 422/502, 503, 504; 156/60, 156/349, 381
See application file for complete search history.

(56) References Cited

U.S. PATENT DOCUMENTS 5,374,564 A    12/1994  Bruel
7,169,251 B2   1/2007   Guo et al.
(Continued)

OTHER PUBLICATIONS

McDonald et al., "Fabrication of microfluidic systems in poly(dimethylsiloxane)," Electrophoresis, 21(1), pp. 27-40 (Jan. 2000).

(Continued)

*Primary Examiner* — Brian J Sines
(74) *Attorney, Agent, or Firm* — Vazken Alexanian; Michael J. Chang, LLC

(57) ABSTRACT

Techniques for use of wafer bonding techniques for sealing of microfluidic chips are provided. In one aspect, a wafer bonding sealing method includes the steps of: forming a first oxide layer coating surfaces of a first wafer, the first wafer having at least one fluidic chip; forming a second oxide layer on a second wafer; and bonding the first wafer to the second wafer via an oxide-to-oxide bond between the first oxide layer and the second oxide layer to form a bonded wafer pair, wherein the second oxide layer seals the at least one fluidic chip on the first wafer. The second wafer can be at least partially removed after performing the bonding, and fluidic ports may be formed in the second oxide layer. A fluidic chip device is also provided.

13 Claims, 6 Drawing Sheets

(51) Int. Cl.
    *B32B 37/00*     (2006.01)
    *H01L 21/20*     (2006.01)
    *B01L 3/00*     (2006.01)
    *B81C 1/00*     (2006.01)
    *B81B 7/00*     (2006.01)
    *G01N 15/10*     (2006.01)

(52) U.S. Cl.
    CPC ............ *B81B 2203/0338* (2013.01); *B81C 2203/0118* (2013.01); *G01N 2015/1081* (2013.01)

(56) References Cited

U.S. PATENT DOCUMENTS

| | | | |
|---|---|---|---|
| 8,652,828 B2 | 2/2014 | Austin et al. | |
| 8,986,966 B2 | 3/2015 | Toner et al. | |
| 2007/0007240 A1* | 1/2007 | Wise et al. | 216/13 |
| 2007/0072330 A1 | 3/2007 | Popa et al. | |
| 2008/0122115 A1* | 5/2008 | Popa et al. | 257/777 |
| 2014/0138351 A1 | 5/2014 | Mancarella et al. | |
| 2014/0154703 A1 | 6/2014 | Skelley et al. | |
| 2015/0093816 A1* | 4/2015 | Lagae et al. | 435/287.2 |

OTHER PUBLICATIONS

Jia et al., "Bonding of Glass microfluidic Chips at Room Temperatures," Anal. Chem., 76, pp. 5597-5602 (Aug. 2004).

Moriceau et al., "Overview of recent direct wafer bonding advances and applications," Advances in Natural Sciences: Nanoscience and Nanotechnology 1(4):043004 (2010) (Published Feb. 2011).

Huang et al., "Continuous Particle Separation Through Deterministic Lateral Displacement," Science, vol. 304 (May 2004).

Schmidt, "Wafer-to-Wafer Bonding for Microstructure Formation," Proceedings of the IEEE, vol. 86, No. 8, Aug. 1998, pp. 1575-1585.

Cao et al., "Fabrication of 10 nm enclosed nanofluidic channels," Applied Physics Letters, vol. 81, No. 1 (Jul. 2002) pp. 174-176.

M. Stjernstrom et al., "Method for fabrication of microfluidic systems in glass," J. Micromech. and Microeng. 8 (1), pp. 33-38 (Mar. 1998)).

\* cited by examiner

DIRECT BOND TRANSFER LAYERS FOR MANUFACTURABLE SEALING OF MICROFLUIDIC CHIPS

FIELD OF THE INVENTION

The present invention relates to microfluidic chips, and more particularly, to wafer bonding techniques for use in sealing of microfluidic chips.

BACKGROUND OF THE INVENTION

There is extensive and growing interest in lab-on-a-chip technologies. Such a broad interest in microfluidic technologies extends from their many advantages over traditional laboratory methods, such as the ability to carry out separation and detection with high resolution and sensitivity, need for only very small quantities of sample and reagent, small footprint of the analytical devices these chips contain, low cost of manufacture, and short time of analysis.

With such great promise, a diverse host of platforms used to house the microfluidic channels and devices have emerged. The result has been a plethora of highly specialized micro/nanofluidic systems each incompatible with the others. Optimally, a universal platform could be developed comprised of functional building blocks—each layer performing a specific function—that could be stacked one on top of the other to rapidly create versatile and highly customizable chips for a particular application, leading to a low-cost development cycle since stacked chips can be connected by a network of fluidic and electrical through silicon vias (TSVs). The road to create such a system requires the ability to fabricate micro/nanofluidic channels and devices that can be manufacturably encapsulated in such a way as to provide a fluid-tight seal for the fluidic channels.

The sealing of fluidic chips has generally been accomplished one of the following ways. Polymer Systems—much of the exploratory research in the field of microfluidics has be carried out using poly(dimethylsiloxane) or PDMS, which is a soft elastomer. Among its primary advantages are its ease of use to create structures using soft lithography and its optical transparency. This material provides an early stage development tool where pattern negatives can be quickly replicated by spinning the material onto structures patterned in resist or other materials that are supported by substrate, and then cured, removed, and bonded to a target substrate without the need for downstream processing. See, for example, McDonald et al., "Fabrication of microfluidic systems in poly(dimethylsiloxane)," Electrophoresis, 21(1), pgs. 27-40 (January 2000). The primary disadvantages of this material are i) that it does not have sufficient chemical and thermal stability for some applications, hence ii) it is also not compatible with advanced semiconductor processing techniques that can add further functionality and scaling.

Glass Bonding—the mechanical stability of silicon and glass make them useful where rigid walls are needed to precisely control dimensions that are not accessible to PDMS fluidic structures. Additionally, silicon offers a process advantage. Very commonly a process, such as anodic bonding, is used to seal glass to pieces of silicon or silicon dioxide covered material that have micro/nanofluidic features defined in them without the need for an adhesion layer that can redefine or constrict fluidic features. The glass acts as a ceiling to hermetically encapsulate the micro-mechanical silicon elements. Typically, glass bonding to silicon is achieved through rigorous and labor intensive cleaning and preparation measures. See, for example, Jia et al., "Bonding of Glass microfluidic Chips at Room Temperatures," Anal. Chem., 76, pgs. 5597-5602 (August 2004). Afterward, pressure must be carefully applied to ensure a good seal without breaking the glass or silicon. Another challenge is that fluidic access holes must be drilled into the glass coverslip to provide an entrance and exit for fluidics flowing into and out of the chip, which is technically challenging on very flat and thin pieces of glass. Finally, long anneals are typically applied to strengthen the glass-silicon or glass-silicon dioxide bond. Glass to glass bonding has also been demonstrated. Nonetheless, none of these approaches provide a clear path to making manufacturable chips at a large scale.

Therefore, improved techniques for sealing of fluidic chips that are fully compatible with three-dimensional integrated silicon technology or chip stacking would be desirable.

SUMMARY OF THE INVENTION

The present invention provides for the use of wafer bonding techniques for sealing of microfluidic chips. In one aspect of the invention, a wafer bonding sealing method is provided. The method includes the steps of: forming a first oxide layer coating surfaces of a first wafer, the first wafer containing at least one fluidic chip (e.g., having fluidic channels joined by a pillar arrangement for particle sorting); forming a second oxide layer on a second wafer; and bonding the first wafer to the second wafer via an oxide-to-oxide bond between the first oxide layer and the second oxide layer to form a bonded wafer pair, wherein the second oxide layer seals the at least one fluidic chip on the first wafer. The second wafer can be at least partially removed after performing the bonding, and fluidic ports may be formed in the second oxide layer to introduce fluids into the chips after singulation. The fluidic ports may be only partially formed through the second oxide layer, such that a portion of the second oxide layer remains separating the fluid ports from the fluid channels to prevent fluid from wetting the channels prior to use and to keep the external ambient environment from chemically modifying the channel surfaces.

In another aspect of the invention, a device is provided which includes: a first oxide layer coating surfaces of a first wafer, the first wafer containing at least one fluidic chip; and a second oxide layer bonded to the first oxide layer via an oxide-to-oxide bond, wherein the second oxide layer seals the at least one fluidic chip on the first wafer. Fluidic ports may be present in the second oxide layer. However, the fluidic ports may (optionally) be only partially formed through the second oxide layer, such that a portion of the second oxide layer remains separating the fluid ports from the fluid channels to prevent fluid from entering the channels prior to use.

A more complete understanding of the present invention, as well as further features and advantages of the present invention, will be obtained by reference to the following detailed description and drawings.

DETAILED DESCRIPTION OF PREFERRED EMBODIMENTS

Provided herein are techniques for sealing micro/nanofluidic channels and features using direct wafer bonding. Advantageously, the present techniques for capping fluidic chips are fully cleanroom compatible to enable high-volume production and three-dimensional integration. As will be described in detail below, a thin thermal oxide is formed on the walls and surface of a first wafer containing the (micro/nano) fluidic features, which provides a good bonding surface for a second wafer consisting of bulk silicon (Si) covered with a thick uniform silicon dioxide ($SiO_2$) layer that becomes the ceiling for the fluidic features and provides a good oxide-to-oxide bond between the two wafers. The two wafers are then tacked together in a wafer bonding tool with the two oxide surfaces in contact and subsequently annealed at a high temperature to fortify the bond. Finally, the silicon of the second wafer is removed. The final microfluidic features can therefore also consist of a high quality $SiO_2$ covering all surfaces, which is easy to modify chemically.

The present wafer bonding approach has several notable advantages over other bonding processes, such as anodic bonding, eutectic bonding, glass fritting, and polymer adhesive bonding. For example, wafer bonding has the ability to survive the high temperatures required to make stacked structures; wafer bonding has a high bond strength; and wafer bonding is compatible with standard microelectronic processing (see for example, Moriceau et al., "Overview of recent direct wafer bonding advances and applications," Advances in Natural Sciences: Nanoscience and Nanotechnology 1(4):043004 (2010) (Published February 2011), the contents of which are incorporated by reference as if fully set forth herein).

Figure 1:
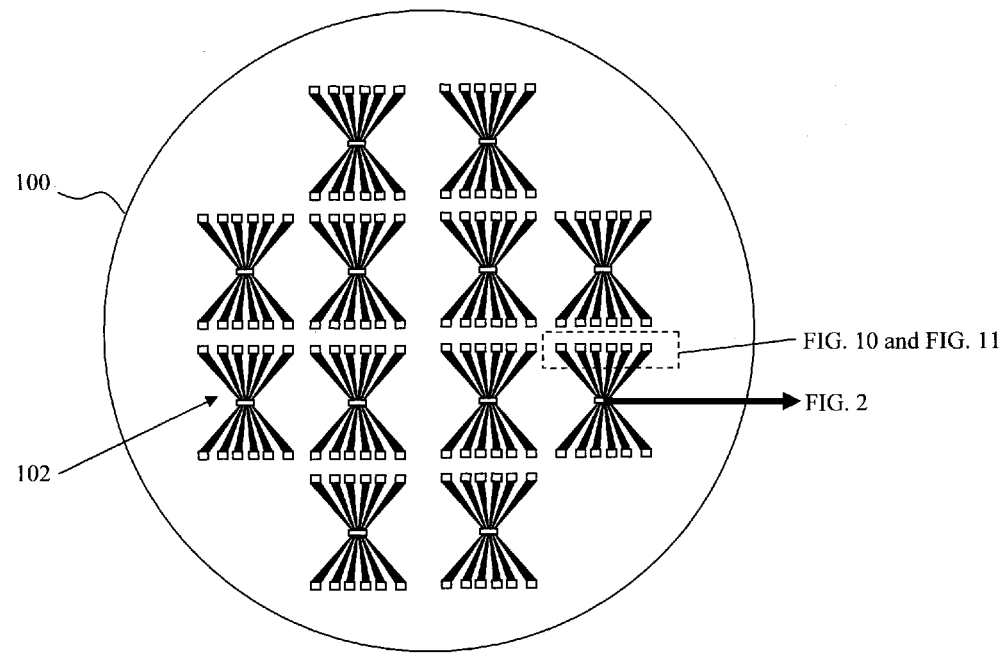
FIG. 1 is a diagram illustrating an exemplary (first) wafer (100) on which one or more fluidic chips (102) have been printed according to an embodiment of the present invention.
Figure 2:
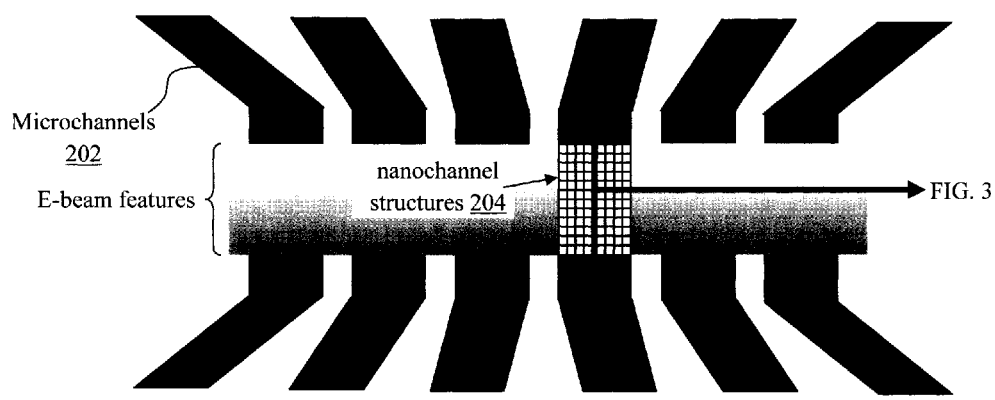
FIG. 2 is a diagram illustrating an enlarged view of one of the fluidic chips (102) which includes one or more microchannels (202) joined by nanochannel structures (204) according to an embodiment of the present invention.

The process begins, as shown in FIGS. 1-4, and shown by way of example with a wafer 100 on which one or more fluidic chips 102 have been printed. In the example shown in FIG. 1, multiple fluidic chips 102 printed on the wafer. This is however only an example, and it is to be understood that the present techniques may be performed in the same manner described for implementations involving a single chip. As will be described in detail below, the present techniques involve a bonding process between a pair of wafers. Wafer 100 is the first wafer in the pair, and thus may also be referred to herein as the first wafer. FIG. 2 provides an enlarged view of one of the fluidic chips 102. As shown in FIG. 2, each of the fluidic chips 102 includes pairs of microchannels 202 joined by nanochannel structures 204. The terms "micro" and "nano" are used herein to denote the relative sizes of features. Regarding the micro/nanochannels for instance, as shown in FIG. 2, the microchannels 202 feed into the relatively smaller nanochannel structures 204. By way of example only, the microchannels can have a width of from 10 micrometers (μm) to about 50 μm, and ranges there between, whereas the nanochannels can have a width of from 30 nanometers (nm) to about 500 nm, and ranges there between.

Figure 3:
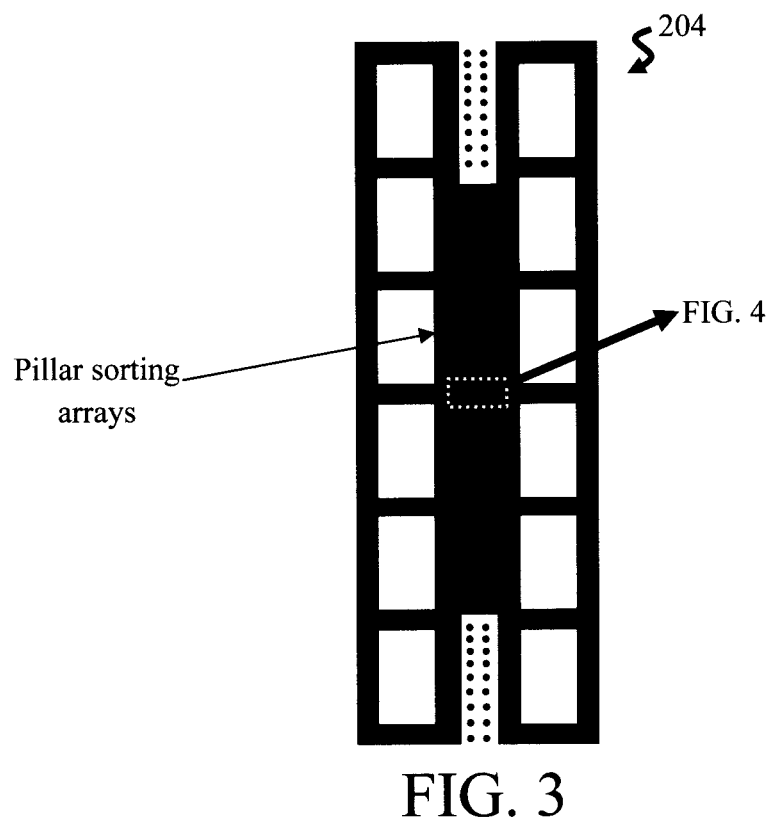
FIG. 3 is a diagram illustrating an enlarged view of one of the nanochannel structures (204) according to an embodiment of the present invention.

An enlarged view of one of the nanochannel structures 204 is shown in FIG. 3. Each of the nanochannel structures 204 contains a pillar arrangement for particle sorting (also referred to herein as a pillar sorting array). The pillar sorting arrays can operate on the principle of deterministic lateral displacement to sort, separate, and enrich microscale and nanoscale particles. See, for example, Huang et al., "Continuous Particle Separation Through Deterministic Lateral Displacement," Science, vol. 304 (May 2004), the contents of which are incorporated by reference as if fully set forth herein.

Figure 4:
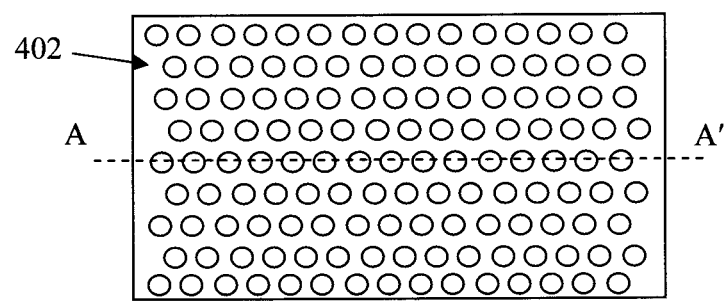
FIG. 4 is a diagram illustrating an enlarged view of one of the pillar sorting arrays (402) according to an embodiment of the present invention.
Figure 5:
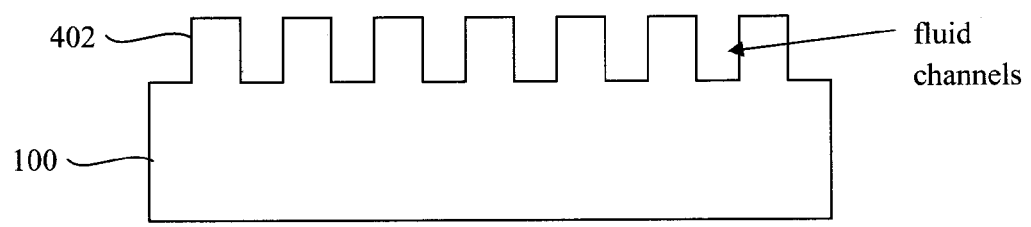
FIG. 5 is a cross-sectional diagram illustrating one of the pillar sorting arrays (402) according to an embodiment of the present invention.

An enlarged view of one of the pillar sorting arrays is provided in FIG. 4. As shown in FIG. 4, the pillar array includes a plurality of (e.g., silicon) pillars 402 patterned in the wafer. FIG. 4 provides a top-down view of the pillar array. In order to better illustrate the present process, reference will now shift to cross-sectional views of the pillar array (e.g., based on a cut along line A-A'—see FIG. 4). See, for example, FIG. 5. As shown in FIG. 5, the pillars 402 define a plurality of fluid channels. It is via these fluid channels that liquid samples will pass through the array. While the following description details the present process from the perspective of sealing fluidic channels in the pillar array, it is to be understood that the instant techniques are employed (in the same manner described) to seal any/all of the channels or features present in this any other silicon and oxide based fluidic chip design. Thus, the channels shown in the figures and described below might generally represent any of the micro/nano fluidic channels present on the chip.

Figure 6:
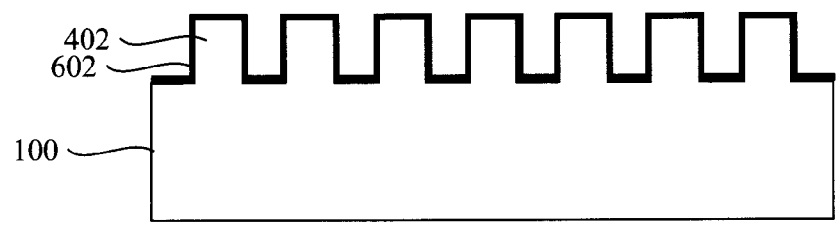
FIG. 6 is a cross-sectional diagram illustrating a (first) thin oxide layer (602) having been formed on the surfaces of the pillar array (402) to help facilitate wafer bonding according to an embodiment of the present invention.

As highlighted above, the present techniques employ novel wafer bonding processes for sealing the above-described fluidic chips. To help facilitate bonding, a thin, conformal oxide layer 602 is formed on the surfaces of the pillar array. See FIG. 6. This oxide layer 602 may also be referred to herein as a (first) bonding oxide layer so as to differentiate it from the (second) oxide layer that will be formed on a second wafer (see below). According to an exemplary embodiment, the oxide layer 602 is formed on the top and sidewall surfaces of the pillars 402 (as shown in FIG. 6) having a thickness of from about 5 nm to about 50 nm, and ranges therebetween. By way of example only, oxide layer 602 can be formed in this manner using a thermal oxidation process. In that case, oxide layer 602 may also be referred to herein as a thermal oxide. In order to form a thin oxide layer 602, it may be preferable to use a dry thermal oxidation process, i.e., wherein molecular oxygen is the oxidant.

Figure 7:
FIG. 7 is a cross-sectional diagram illustrating a (second) wafer (700) having a (second) oxide layer (702) formed thereon according to an embodiment of the present invention.

As highlighted above, the present wafer bonding process will involve providing a second wafer 700, also having a bonding oxide layer, and bonding the first wafer 100 to the second wafer 700 via an oxide-to-oxide bond between the respective bonding oxide layers. Thus, as shown in FIG. 7, a (second) wafer 700 is provided, and a (second) oxide layer 702 is formed on the wafer 700. Since the (second) wafer 700 will be used to provide the physical ceiling oxide used to seal the fluid channels, wafer 700 may also be referred to herein as the ceiling wafer, so as to distinguish it from wafer 100 containing the fluid channels.

According to an exemplary embodiment, wafer 700 is a bulk silicon (Si) wafer having a thickness of from about 550 micrometers ($\mu m$) to about 750 $\mu m$, and ranges therebetween. A thermal oxidation process may be used here as well to form the oxide layer 702 on the wafer 700. However, the oxide layer 702 is formed thicker than oxide layer 602 (i.e., a thicker oxide layer 702 can enhance the oxide-to-oxide bond and is necessary to provide a robust seal that can withstand pressure applied to the channels to drive fluidics, while one runs the risk of occluding trenches in the first wafer with a thicker oxide layer 602). By way of example only, oxide layer 702 can be formed on the wafer 700 to a thickness of from about 0.5 $\mu m$ to about 2 $\mu m$, and ranges therebetween. A wet thermal oxidation process (e.g., using water vapor as the oxidant) is well suited for growing thicker oxide layers. As will be apparent from the description that follows, the oxide layer 702 on wafer 700 will serve as the ceiling for the fluidic channels (on wafer 100).

Prior to forming the oxide layer 702 on wafer 700, it is preferable to clean the wafer 700 to remove any potential contaminants. By way of example only, a standard RCA clean may be performed to remove organic and other contaminants from the surface of the wafer 700. Further, prior to bonding the wafers together, it is preferable to clean the oxide bonding surfaces. By way of example only, a distilled water megasonic cleaning, and subsequent infrared (IR) drying of the wafers 100 and 700 can be performed post formation of the oxide layers 602 and 702 before tacking the wafers together for bonding.

Figure 8:
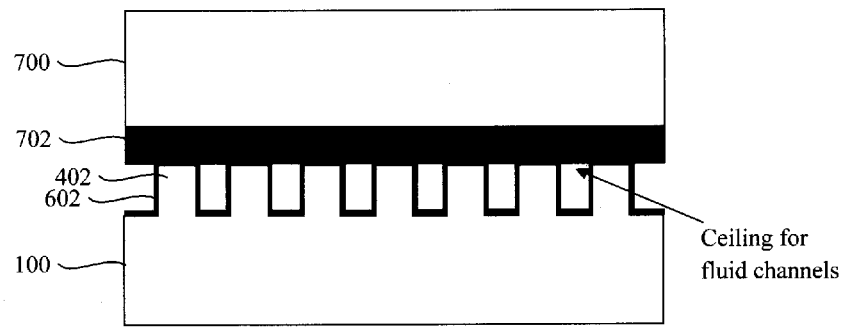
FIG. 8 is a cross-sectional diagram illustrating the first wafer (100) and the second wafer (700) having been bonded together by way of an oxide-to-oxide bond between the first (602) and second (702) oxide layers according to an embodiment of the present invention.

Wafers 100 and 700 are then bonded together by way of a direct oxide-to-oxide bond between oxide layers 602 and 702, forming a bonded wafer pair. See FIG. 8. According to an exemplary embodiment, the bonding process is performed by pressing the (bonding) oxide layers 602 and 702 together (using a bonding tool) at room temperature with a force initiating from a center contacting area. The contacting area will expand from the center outward across the layers. Thereafter, a thermal anneal at from about 800° C. to about 1,000° C., and ranges therebetween, for a duration of from about 40 minutes to about 60 minutes, and ranges therebetween in an inert gas (e.g., nitrogen ($N_2$)) ambient is used to enforce the bonding quality. By way of example only, a suitable bonding tool is the CL-200 substrate bonder available from SUSS MicroTec AG, Garching, Germany. As shown in FIG. 8, the oxide layer 702 (originating on the second wafer 700) now serves as the ceiling of the fluid channels.

Figure 9:
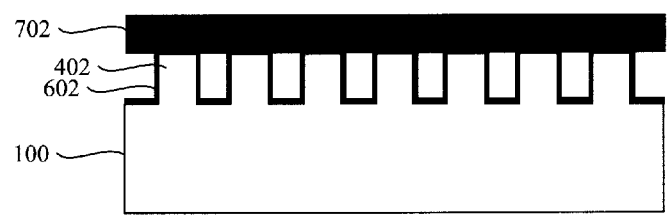
FIG. 9 is a cross-sectional diagram illustrating the (second) wafer (700) having been removed leaving behind only the (second) oxide layer (702) over/sealing the channels according to an embodiment of the present invention.

Following wafer bonding, according to an exemplary embodiment, the (second) wafer 700 is removed from the structure leaving behind only the (second) oxide layer 702 over and sealing the channels. See FIG. 9. For instance, the thickness of wafer 700 is first reduced (e.g., to about 50 $\mu m$) using a coarse followed by a thin wafer polish process via chemical mechanical polishing (CMP). Alternatively, a Smart Cut™ process may be employed in the same manner to partially remove the wafer 700. The Smart Cut™ process is described, for example, in U.S. Pat. No. 5,374,564 issued to Bruel, entitled "Process for the Production of Thin Semiconductor Material Films," the contents of which are incorporated by reference as if fully set forth herein. The remaining portion of wafer 700 can then be removed using a tetramethylammonium hydroxide (TMAH) etch process to leave only the (from about 0.5 $\mu m$ to about 2 $\mu m$, and ranges therebetween—see above) thick oxide layer 702 ceiling bonded directly to the pillar array of wafer 100. It is notable that the thin oxide layer 602 serves to prevent any etching of wafer 100 during the TMAH etch. As an alternative to TMAH, potassium hydroxide (KOH) wet etching or xenon difluoride ($XeFl_2$) etching may also be employed to remove the remaining portions of wafer 100.

Figure 10:
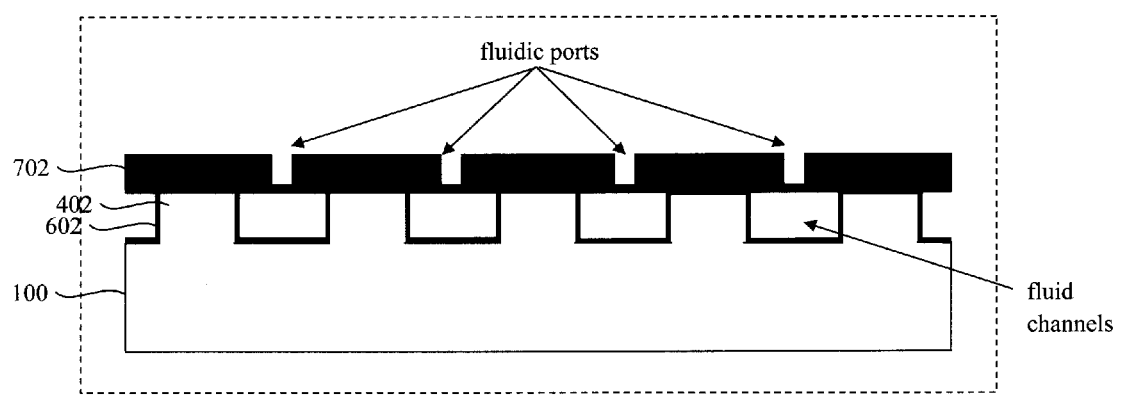
FIG. 10 is a cross-sectional diagram illustrating fluidic ports having been formed in the second oxide layer (702) according to an embodiment of the present invention.
Figure 11:
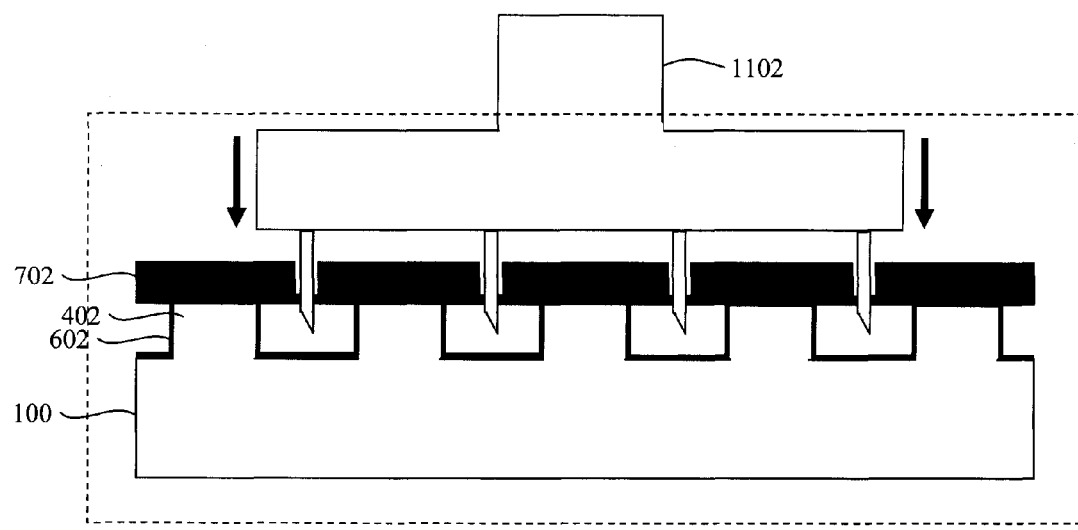
FIG. 11 is a cross-sectional diagram illustrating a microfluidic jig (1102) being used to open a partially formed fluidic port just prior to use according to an embodiment of the present invention.
Figure 12:
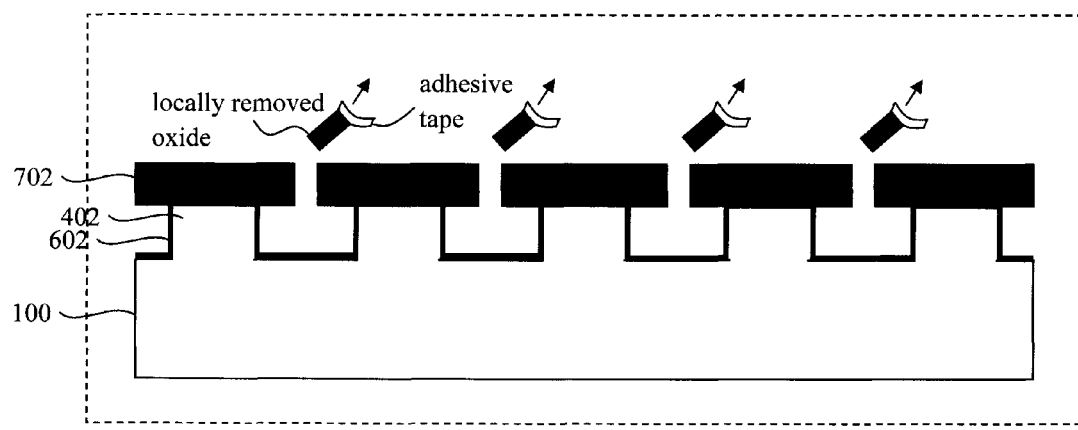
FIG. 12 is a cross-sectional diagram illustrating an alternative technique for forming fluidic ports using an adhesive tape according to an embodiment of the present invention.

Advantageously, the present ceiling techniques enable further processing not possible with conventional configurations (such as those using glass to seal the channels). For instance, as shown in FIG. 10, fluidic ports can be formed in the oxide layer 702 to access the channels. It is notable that the fluidic ports are preferably formed at the ends of the microchannel regions (i.e., the fluidic ports reside in the regions represented by open squares around the perimeter of each chip in FIG. 1). The reason for this is that the channels are much wider in these regions than in the pillar regions, making the oxide much simpler to puncture. Thus, the views in FIGS. 10 and 11 depict the highlighted regions in FIG. 1 (the regions at the ends of the microchannel regions). The fluidic ports can be formed using a standard lithography and etching process (such as reactive ion etching or RIE). The fluidic ports can be formed completely through the (ceiling) oxide layer 702 or, as shown in FIG. 10, the fluidic ports can be formed extending only partway through the (ceiling) oxide layer 702. By only partially forming the fluidic ports, a part of the oxide layer 702 will remain over the channels preventing any fluid from entering the channels prior to use via wicking or capillary action. The thin remaining oxide can then be punctured by a needle embedded within a microfluidic jig, such that the oxide is penetrated and the microfluidic channels opened just prior to use. According to an exemplary embodiment, the fluidic ports are partially formed through the oxide layer 702 (such as shown in FIG. 10) leaving a portion of the oxide layer having a thickness of from about 50 nm to about 300 nm, and ranges therebetween, separating the fluidic ports and the channels.

FIG. 11 illustrates the optional use of a microfluidic jig 1102 to fully open up the (partially formed) fluidic ports prior to use. As shown in FIG. 11, the microfluidic jig 1102 contains a needle(s) that can pierce the thin remaining portion of the (ceiling) oxide layer 702 to gain access to the channels just prior to use.

Alternatively, an adhesive tape may be applied in the desired area of the fluidic port regions, where ports have not been preetched to form any fluidic ports. Then, just prior to use, the adhesive tape can be peeled off (and with it local portions of the ceiling oxide layer 702) which will locally remove oxide in these regions forming the fluidic ports.

Figure 13:
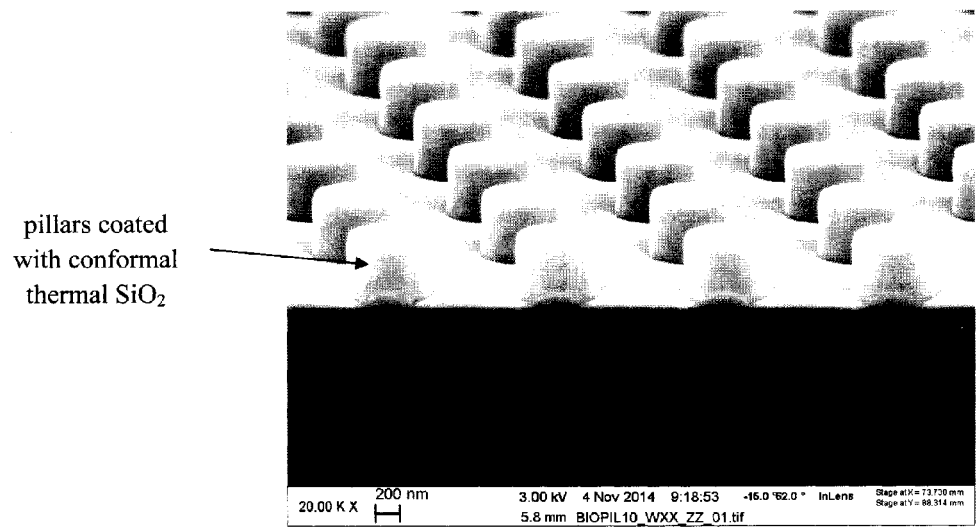
FIG. 13 is an image of a silicon (Si) pillar array sample prepared by the present techniques to have 50 nanometers (nm) of thermally grown silicon dioxide ($SiO_2$) on the surface according to an embodiment of the present invention.
Figure 14:
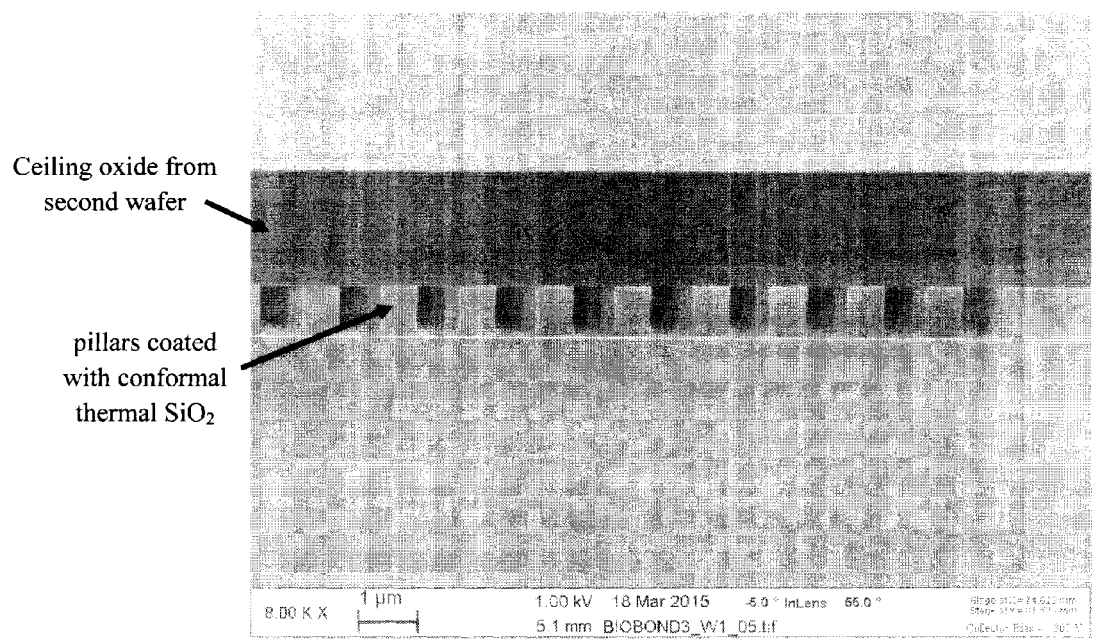
FIG. 14 is an image of the Si pillar array of FIG. 12 having been sealed using the present direct wafer bond transfer process according to an embodiment of the present invention.

The present techniques are further illustrated by way of reference to the following non-limiting examples. FIG. 13 illustrates an uncapped Si pillar array having 50 nm of thermally grown $SiO_2$ on the surface prepared using the present techniques. FIG. 14 illustrates a processed sealed array using the direct wafer bond transfer process described above. In this example, the ceiling oxide (provided via the second wafer) was a 2 μm thick layer of $SiO_2$.

Lithography and anisotropic RIE of the ceiling $SiO_2$ in select regions was then used to establish fluidic ports (not shown in the images) to access the microfluidic channels and a protective layer, such as a spin applied photoresist when fluidic ports have not be RIE etched completely through the ceiling oxide (702), or bonding tape for dicing when holes are etched completely through to the microchannels, was then added for wafer dicing to separate the individual chips. These chips ran fluidics containing sub-micron particles demonstrating fully functional sorting capabilities at high pressure and withstood over 20 Bars of fluidic pressure without leakage or damage to the oxide during stress tests, which is far more than is typically employed in microfluidic applications.

Although illustrative embodiments of the present invention have been described herein, it is to be understood that the invention is not limited to those precise embodiments, and that various other changes and modifications may be made by one skilled in the art without departing from the scope of the invention.

What is claimed is:

1. A wafer bonding sealing method, comprising the steps of:
    forming a first oxide layer coating surfaces of a first wafer, the first wafer comprising at least one fluidic chip having fluidic channels joined by nanochannel structures, wherein each of the nanochannel structures comprises an arrangement of pillars for particle sorting, and wherein the first oxide layer is formed conformally on top and sidewall surfaces of each of the pillars;
    forming a second oxide layer on a second wafer; and
    bonding the first wafer to the second wafer via an oxide-to-oxide bond between the first oxide layer and the second oxide layer to form a bonded wafer pair, wherein the second oxide layer seals the at least one fluidic chip on the first wafer.

2. The method of claim 1, wherein the first oxide layer has a thickness of from about 5 nm to about 50 nm, and ranges therebetween.

3. The method of claim 1, wherein the second oxide layer has a thickness of from about 0.5 μm to about 2 μm, and ranges therebetween.

4. The method of claim 1, further comprising the step of:
    at least partially removing the second wafer after performing the bonding.

5. The method of claim 1, further comprising the step of:
    fully removing the second wafer after performing the bonding.

6. The method of claim 1, further comprising the step of:
    forming fluidic ports in the second oxide layer over ends of the fluidic channels.

7. The method of claim 6, wherein the fluidic ports are partially formed through the second oxide layer, the method further comprising the step of:
    etching each of the fluidic ports partway through the second oxide layer so as to leave a portion of the second oxide layer separating the fluid ports from the fluidic channels.

8. The method of claim 7, further comprising the step of:
    fully opening the partially formed fluidic ports just prior to use by way of a microfluidic jig comprising needles for piercing the portion of the second oxide layer separating the fluid ports from the fluidic channels.

9. The method of claim 6, further comprising the steps of:
    applying pieces of an adhesive tape selectively to local portions of the second oxide layer where the fluidic ports are to be formed; and
    peeling off the pieces of the adhesive tape just prior to use to locally remove portions of the second oxide layer forming the fluidic ports.

10. The method of claim 1, wherein the step of bonding the first wafer to the second wafer comprises the step of:
    annealing the first wafer and the second wafer at a temperature of from about 800° C. to about 1,000° C., and ranges therebetween, for a duration of from about 40 minutes to about 60 minutes, and ranges therebetween, to enforce bonding quality.

11. The method of claim 10, wherein the annealing is performed in a nitrogen ambient.

12. The method of claim 1, wherein at least one of the first oxide layer and the second oxide layer comprises a thermal oxide.

13. The method of claim 7, wherein the portion of the second oxide layer left separating the fluid ports from the fluidic channels has a thickness of from about 50 nm to about 300 nm, and ranges therebetween.

* * * * *